(12) United States Patent
Yonehara et al.

(10) Patent No.: US 8,021,855 B2
(45) Date of Patent: Sep. 20, 2011

(54) METHOD OF DECOMPOSING PROTEIN WITH SULFONIC ACID COMPOUND

(75) Inventors: Satoshi Yonehara, Kyoto (JP); Kaori Ishimaru, Kyoto (JP); Kaoru Hirai, Kyoto (JP)

(73) Assignee: ARKRAY Inc., Kyoto (JP)

( * ) Notice: Subject to any disclaimer, the term of this patent is extended or adjusted under 35 U.S.C. 154(b) by 578 days.

(21) Appl. No.: 10/521,234

(22) PCT Filed: Apr. 28, 2003

(86) PCT No.: PCT/JP03/05487
§ 371 (c)(1),
(2), (4) Date: Jan. 13, 2005

(87) PCT Pub. No.: WO2004/007760
PCT Pub. Date: Jan. 22, 2004

(65) Prior Publication Data
US 2005/0260735 A1   Nov. 24, 2005

(30) Foreign Application Priority Data
Jul. 17, 2002   (JP) ................................. 2002-208305

(51) Int. Cl.
*C12Q 1/26*   (2006.01)
(52) U.S. Cl. .............................. 435/25; 435/28; 435/23
(58) Field of Classification Search ........................ None
See application file for complete search history.

(56) References Cited

U.S. PATENT DOCUMENTS

| | | | |
|---|---|---|---|
| 4,102,810 A * | 7/1978 | Armstrong | 436/16 |
| 4,119,405 A | 10/1978 | Lam | |
| 4,265,810 A * | 5/1981 | Bauman et al. | 534/558 |
| 4,310,626 A | 1/1982 | Burkhardt et al. | |
| 4,587,220 A | 5/1986 | Mayambala-Mwanika et al. | |
| 4,743,559 A | 5/1988 | Koever et al. | |
| 4,755,472 A | 7/1988 | Ismail et al. | |
| 4,954,451 A | 9/1990 | Albarella et al. | |
| 5,468,640 A * | 11/1995 | Benezra et al. | 436/66 |
| 5,677,272 A | 10/1997 | Ghosh et al. | |
| 5,731,206 A * | 3/1998 | Ledis et al. | 436/17 |
| 5,810,944 A | 9/1998 | Smitkowski et al. | |
| 5,902,731 A | 5/1999 | Ouyang et al. | |
| 6,127,138 A * | 10/2000 | Ishimaru et al. | 435/23 |
| 6,200,773 B1 | 3/2001 | Ouyang et al. | |
| 6,790,665 B2 * | 9/2004 | Yonehara et al. | 436/66 |
| 2002/0025546 A1 | 2/2002 | Komori et al. | |
| 2002/0173043 A1 | 11/2002 | Merabet et al. | |
| 2003/0162242 A1 | 8/2003 | Yonehara | |
| 2004/0063213 A1 | 4/2004 | Hirai et al. | |
| 2005/0221415 A1* | 10/2005 | Yonehara et al. | 435/25 |

FOREIGN PATENT DOCUMENTS

| | | |
|---|---|---|
| EP | 0 158 964 A2 * | 10/1985 |
| EP | 1 002 874 A2 * | 5/2000 |
| EP | 1002874 A2 * | 5/2000 |
| EP | 1 362 925 | 11/2003 |
| JP | 56-151358 | 11/1981 |
| JP | 57-13357 | 1/1982 |
| JP | 57-161650 | 10/1982 |
| JP | 59-193354 | 11/1984 |
| JP | 60-168050 | 8/1985 |
| JP | 61-000084 A | 1/1986 |
| JP | 62-169053 | 7/1987 |
| JP | 2-69644 | 3/1990 |
| JP | 3-30697 | 2/1991 |
| JP | 9-185021 | 7/1997 |
| JP | 10-210967 | 8/1998 |
| JP | 11-196897 | 7/1999 |
| JP | 2001-292795 A | 10/2001 |
| WO | 02/06519 | 1/2002 |
| WO | 02/27331 | 4/2002 |
| WO | 02/061119 | 8/2002 |

OTHER PUBLICATIONS

Oshiro et al., 1982, Clin. Biochem. vol. 15, No. 1, p. 83-88.*
Johnson et al., 1994, Blood, vol. 83, No. 4, p. 1117-1123.*
PAC, 1995, 67, 1307, Glossary of class names of organic compounds, pp. 1351 and 1369.*
Johnson et al., Blood, 1994, vol. 83, No. 4, p. 1117-1123.*
Cosoveanu et al. , Journal of Chromatography A, 1996, vol. 727, p. 324-329.*
Goodwin, et al., "Quantification of Protein Solutions with Trinitrobenzenesulfonic Acid", Clinical Chemistry, vol. 16, No. 1, 1970.
Oshiro, et al., New Method for Hemoglobin Determination by Using Sodium Lauryl Sulfate (SLS)., Clin. Biochem, 15 (1), 1982.
Gehle, MD, et al "Case Studies Environmental Medicine: Nitrate/Nitrite Toxicity", U.S. Department of Health and Human Services, Course: SS3054, 2001.
"Methemoglobinemia Primary Industrial Chemicals and Non-Occupational Exposures", www.haz-map.com/methem.html. Gajjar, et al., "Activation and Stabilization of Enzymes Entrapped into reversed Micelles: Studies on Hydrolyzing Enzymes—Protease and α-Amylase", Applied Biochemistry and Biotechnology, vol. 49, 1994, pp. 101-112.
Sidelmann, et al., "The effect of chemical anti-inhibitors on fibrinolytic enzymes and inhibitors", Clinics Chimica Acta 261, 1997 43-56.
Stennicke, et al., "biochemical Characteristics of Caspases-3, -6, -7, and -8", The Journal of Biological Chemistry, vol. 272, No. 41, Issue of Oct. 10, pp. 25719-25723, 1997 (XP-002146144).

* cited by examiner

*Primary Examiner* — Kade Ariani
(74) *Attorney, Agent, or Firm* — Morgan, Lewis & Bockius LLP

(57) ABSTRACT

A method of assaying a glycated protein in a sample with the use of redox reaction, in which highly reliable measurement can be obtained. A sample containing a glycated protein is treated with protease in the presence of a sulfonic acid compound, so that the glycated protein is degraded. The glycated portion of the resultant glycated protein degradation product is reacted with fructosyl amino acid oxidase, and this redox reaction is measured, thereby determining the amount of glycated protein. Sodium lauryl sulfate can be used as the sulfonic acid compound.

3 Claims, No Drawings

METHOD OF DECOMPOSING PROTEIN WITH SULFONIC ACID COMPOUND

TECHNICAL FIELD

The present invention relates to a method of degrading proteins, and a method of treating glycated proteins in a sample with a protease and determining the amount of the glycated proteins using a redox reaction.

BACKGROUND ART

Conventionally, in order to detect a target protein (including a peptide) in a sample or deactivate a function of the protein that affects measurements, a method of degrading the protein with a protease has been applied in various measuring methods.

For example, an attempt is now being made to measure, by an enzymatic method, glycated proteins in blood cells, which serve as a significant indicator in the diagnosis, therapy and the like of diabetes, especially, glycated hemoglobin in erythrocytes, which reflects the patient's past history of blood glucose levels. In this case, the method of degrading the glycated proteins with the protease also is used. In the enzymatic method, a fructosyl amino acid oxidase (hereinafter, referred to as "FAOD") is allowed to act on a glycated portion of the glycated protein in a hemolyzed sample, thus generating hydrogen peroxide. The amount of this hydrogen peroxide corresponds to the amount of the glycated protein. Then, a peroxidase (hereinafter, referred to as "POD") and a substrate that develops color by oxidation are added to the sample that has been treated with FAOD, so that a redox reaction occurs between the hydrogen peroxide and the substrate with the POD as a catalyst. At this time, since the substrate develops color when it is oxidized, the amount of the hydrogen peroxide can be determined by measuring the color developed. As a result, the amount of the glycated protein in the sample can be determined.

However, the FAOD to be allowed to act on the glycated portion acts on a glycated amino acid and a shorter glycated peptide fragment more easily than on a glycated protein and a glycated peptide. Accordingly, by degrading the glycated protein and the glycated peptide in advance with a protease so that the FAOD can act on the glycated portion more easily, the accuracy of measurement is improved.

However, since the protease has a substrate specificity and shows different degrading activities depending on the substrate to be treated, there is a problem that, depending on the kind of a target protein, the degradation may take a long time and the measurement cannot be carried out quickly. Further, when the target protein is glycated as in the case of the above-mentioned glycated protein, it sometimes is difficult to degrade due to its steric hindrance and the like. For this reason, when measuring the glycated protein in the above-mentioned manner, for example, the measurement process as a whole also takes a long time owing to the protease treatment carried out in advance. Therefore, from the viewpoint of applicability in the field of clinical tests etc., there has been a demand for a method by which the glycated protein can be measured more quickly.

DISCLOSURE OF INVENTION

Accordingly, it is an object of the present invention to provide a method of producing a protein degradation product by which a protein is degraded quickly and efficiently, and a method of degrading a glycated protein in a sample and determining the amount of the glycated protein.

In order to achieve the above-mentioned object, a method of producing a protein degradation product according to the present invention includes treating a protein with a protease in the presence of a sulfonic acid compound. In the present invention, the "protein" also includes a peptide, and the "protein degradation product" includes a degradation product of the above-mentioned peptide.

The protease treatment in the presence of the sulfonic acid compound in this manner makes it possible to degrade a protein in a sample quickly.

Next, a method of measuring a glycated protein according to the present invention, in which an amount of the glycated protein is determined by treating a sample containing the glycated protein with a protease so as to degrade the glycated protein, allowing a glycated portion of a glycated protein degradation product obtained by the degradation and a FAOD to react with each other, and measuring this redox reaction, includes carrying out the protease treatment in the presence of a sulfonic acid compound. Incidentally, the "glycated protein" in the present invention also includes a glycated peptide.

In a conventional method carried out in the absence of a sulfonic acid compound, a protease treatment as long as, for example, about 6 to 40 hours has been necessary for degrading the glycated protein sufficiently with the protease so as to allow FAOD to act on the glycated portion easily. Accordingly, the above-mentioned enzymatic method requires a long time to measure the glycated protein and thus is not very useful. In contrast, according to the measuring method of the present invention, since it is possible to degrade a glycated protein or the like within a short period, a glycated protein or the like can be measured quickly. For example, under the same conditions as in the conventional method except that a sulfonic acid compound is added, the measuring method of the present invention can shorten the time required for the measurement to about 1/10 to 1/2000 of that in the case where no sulfonic acid compound is present. Consequently, the measuring method according to the present invention achieves a still quicker and more accurate measurement, which is useful for various tests in clinical medicine as described above.

BEST MODE FOR CARRYING OUT THE INVENTION

In the method of producing a protein degradation product and the method of measuring a glycated protein according to the present invention, the sulfonic acid compound can be a compound represented by, for example, a general formula: $R-SO_3X$.

In the above formula, X is, for example, Na, K, Li, H or the like, and R preferably is a hydrophobic group, for example, $CH_3(CH_2)_n-$, $CH_3(CH_2)_n-C_6H_4-$, $C_6H_5-$, $C_6H_5-N=N-C_6H_4-$, $C_6H_5-CH=CH-C_6H_4-$ or the like. For example, n in the above R ranges from 1 to 20. In the above R, "H" may be substituted by an acyl group, a nitro group, a nitroso group, a phenyl group, an alkyl group, an alkyl ether group or the like.

Specific examples of the sulfonic acid compound include, for example, sodium lauryl sulfate (hereinafter, referred to as "SLS"), dodecylbenzenesulfonic acid sodium salt (hereinafter, referred to as "SDBS"), lithium lauryl sulfate (hereinafter, referred to as "LiLS"), 4-aminoazobenzene-4'-sulfonic acid sodium salt (hereinafter, referred to as "ABSA"), 4-amino-4'-nitrostilbene-2,2'-disulfonic acid disodium salt (hereinafter, referred to as "ANDS"), 4,4'-diazidostilbene-2,2'-disulfonic acid disodium salt (hereinafter, referred to as "DADS"), N-cyclohexyl-2-aminoethane sulfonic acid, N-cyclohexyl-3-aminopropane sulfonic acid, N-cyclohexyl-2-hydroxy-3-aminopropane sulfonic acid, piperazine-1,4-bis(2-ethane sulfonic acid), bathophenanthroline sulfonic acid and the like, and the sulfonic acid compound more preferably is SLS, SDBS or LiLS.

Since these sulfonic acid compounds generally have a high solubility, they can be treated easily even when the concentration of glycated proteins in the sample is high. Also, in view of their inexpensiveness, the sulfonic acid compounds are very useful.

Further, in the producing method and the measuring method according to the present invention, it is preferable to carry out a protease treatment in the presence of both the sulfonic acid compound and a nitro compound because the degradation of the glycated protein can be accelerated further.

The above-noted nitro compound is not particularly limited but can be, for example, a nitrobenzene compound or a dinitrobenzene compound. A benzene ring of these compounds preferably has not only the nitro group but also a substituent such as $-NH_2$, $-OH$, $-COOH$, $-SO_3$ or $-(CH_2)_n CH_3$ (n=2 to 9). The substituent also can be, for example, a halogen group, an ether group or a phenyl group.

Specific examples of the nitro compound include, for example, 2,4-dinitrophenol (2,4-DNP), 2,5-dinitrophenyl, 2,6-dinitrophenyl, 4,6-dinitro-2-methyl phenol, 2-amino-4-nitrophenol, 2-amino-5-nitrophenol, 2-amino-4-nitrophenol, p-nitrophenol (p-NP), 2,4-dinitroaniline (2,4-DNA), p-nitroaniline (p-NA), sodium nitrite ($NaNO_2$), potassium nitrite ($KNO2$), 4-amino-4'-nitrostilbene-2,2'-disulfonic Acid Disodium Salt (hereinafter, referred to as "ANPS"), nitrobenzene and the like. When both of the sulfonic acid compound and the nitro compound are present as described above, the combination thereof is not particularly limited.

In the producing method and the measuring method according to the present invention, the protease is not particularly limited but can be, for example, serine proteases, thiol proteases, metalloproteinases or the like. More specifically, it is preferable to use trypsin, proteinase K, chymotrypsin, papain, bromelain, subtilisin, elastase, aminopeptidase and the like. In the case where the glycated protein to be degraded is glycated hemoglobin, it is more preferable to use as the protease a protease degrading the glycated hemoglobin selectively, e.g., bromelain, papain, trypsin derived from porcine pancreas, metalloproteinase and protease derived from *Bacillus subtilis*. Examples of the protease derived from *Bacillus subtilis* include Protease N (trade name, manufactured by Fluka Chemie AG, for example), Protease N "AMANO" (trade name, manufactured by Amano Enzyme Inc.) and the like. Examples of the metalloproteinase include the metalloproteinase (EC 3. 4. 24. 4) derived from the genus *Bacillus* and the like. Among these, metalloproteinase, bromelain and papain are more preferable, and metalloproteinase is most preferable. By using the protease that allows a selective degradation as above, a degradation product of a specific glycated protein can be prepared selectively.

As described above, the method of producing a protein degradation product according to the present invention is characterized by treating a protein with a protease in the presence of a sulfonic acid compound.

The amount of the sulfonic acid compound to be added is not particularly limited but can be determined suitably according to, for example, the kind and added amount of the protease, the kind of sample, the amount of proteins contained in the sample or the like.

More specifically, the sulfonic acid compound is added preferably in the range of 0.01 to 1000 μmol, more preferably in the range of 0.03 to 200 μmol and particularly preferably in the range of 0.05 to 40 μmol with respect to 1 μL of the sample.

In the case of adding both the sulfonic acid compound and the nitro compound, the sulfonic acid compound is added preferably in the range of 0.005 to 20 μmol and the nitro compound is added preferably in the range of 0.005 to 25 μmol, and the former is added more preferably in the range of 0.02 to 4 μmol and the latter is added more preferably in the range of 0.01 to 5 μmol with respect to 1 μl of the sample.

The conditions of the protease treatment are not particularly limited but preferably are set according to the optimal conditions of an enzyme to be used, for example. When the protease is metalloproteinase, the temperature ranges from 10° C. to 37° C. and the treating period ranges from 30 seconds to 60 minutes. It is preferable that the temperature ranges from 20° C. to 37° C. and the treating period ranges from 30 seconds to 10 minutes, and it is more preferable that the former ranges from 25° C. to 37° C. and the latter ranges from 30 seconds to 5 minutes.

Next, as described above, the method for measuring a glycated protein according to the present invention, in which an amount of the glycated protein is determined by treating a sample containing the glycated protein with a protease so as to degrade the glycated protein, allowing a glycated portion of a glycated protein degradation product obtained by the degradation and a fructosyl amino acid oxidase to react with each other, and measuring this redox reaction, includes carrying out the protease treatment in the presence of a sulfonic acid compound.

In the measuring method of the present invention, the amount of the sulfonic acid compound to be added is not particularly limited but can be determined suitably according to, for example, the kind and added amount of the protease, the kind of a sample, the amount of glycated proteins contained in the sample or the like.

More specifically, the sulfonic acid compound is added preferably in the range of 0.01 to 1000 μmol, more preferably in the range of 0.03 to 200 μmol and particularly preferably in the range of 0.05 to 40 μmol with respect to 1 μL of the sample.

In the case of adding both the sulfonic acid compound and the nitro compound, the sulfonic acid compound is added preferably in the range of 0.005 to 20 μmol and the nitro compound is added preferably in the range of 0.005 to 25 μmol, and the former is added more preferably in the range of 0.02 to 4 μmol and the latter is added more preferably in the range of 0.01 to 5 μmol with respect to 1 μl of the sample.

In the measuring method of the present invention, there is no particular limitation on the samples. Other than blood samples such as whole blood, plasma, serum and blood cells, the samples can be, for example, biological samples such as urine, spinal fluid and saliva, drinks such as juices, or foods such as soy sauce and Worcestershire sauce. Among the above, blood samples such as whole blood and blood cells are preferable.

The analyte in the present invention, namely, the glycated protein to be degraded with the protease is, for example, glycated hemoglobin, glycated albumin or the like, and among them, preferably is glycated hemoglobin. Since hemoglobin in blood has a concentration of as high as about 60 to 200 g/L and thus is difficult to degrade, the protease treatment has taken several hours to several days. The measuring method of the present invention makes it possible to carry out the protease treatment within, for example, 20 seconds to 2 hours, allowing quick measurement of the glycated hemoglobin.

Additionally, in the measuring method according to the present invention, it is preferable to carry out a protease treatment in the presence of not only the sulfonic acid compound but also the nitro compound because the degradation of the glycated protein can be accelerated further.

In the measuring method according to the present invention, it is preferable that the redox reaction is measured by determining an amount of hydrogen peroxide generated by the reaction of the glycated portion of the glycated protein and the FAOD. It is also preferable that this amount of the hydrogen peroxide is determined by using an oxidase such as POD to reduce the generated hydrogen peroxide and oxidize a substrate that develops color by oxidation (hereinafter, referred to as a "color-developing substrate") and measuring a degree of the color that the substrate has developed.

The color-developing substrate is not particularly limited but can be, for example, color-developing substrates as listed below. These color-developing substrates usually have an absorbance at 400 nm or longer. On the other hand, the sulfonic acid compound and the nitro compound described above generally do not have an absorbance at 400 nm or longer, so that there is no need to worry about the error caused in the measurement even when used with these color-developing substrates.

More specifically, the color-developing substrate can be, for example, N-(carboxymethylaminocarbonyl)-4,4'-bis(dimethylamino)diphenylamine sodium salt (hereinafter, referred to as "DA-64"), a combination of Trinder's reagent and 4-aminoantipyrine, N,N,N',N',N'',N''',-hexa(3-sulfopropyl)-4,4',4''-triaminotriphenylmethane hexasodium salt (hereinafter, referred to as "TPM-PS"), N,N,N',N',N''', N'''-hexa(2-hydroxy-3-sulfopropyl)-4,4',4''-triaminotriphenylmeth ane hexasodium salt (hereinafter, referred to as "TPM-OS"), 10-(carboxymethylaminocarbonyl)3,7-bis(dimethylamino) phenothiazine sodium salt (hereinafter, referred to as "DA-67"), 10-(methylaminocarbonyl)3,7-bis(dimethylamino) phenothiazine (hereinafter, referred to as "MCDP"), 10-(carboxyaminomethyl-4-benzaminocarbonyl) 3,7-bis(dimethylamino)phenothiazine sodium salt (hereinafter, referred to as "MMX") or the like. Among the above, triaminotriphenylmethane-based color-developing substrates are preferable, for example.

The Trinder's reagent can be, for example, phenols, phenol derivatives, aniline derivatives, naphthols, naphthol derivatives, naphthylamine or naphthylamine derivatives. The compound to be combined with the Trinder's reagent may be not only 4-aminoantipyrine noted above but also, for example, aminoantipyrine derivatives, vanillin diamine sulfonic acid, methyl benzothiazolinone hydrazone (MBTH), sulfonated methyl benzothiazolinone hydrazone (SMBTH) or the like.

In the present invention, it is preferable that the FAOD is a FAOD catalyzing a reaction represented by Formula (1) below.

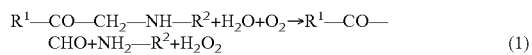

In Formula (1), $R^1$ represents a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by

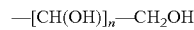

where n is an integer of 0 to 6.

In Formula (1), $R^2$ is not particularly limited. However, when the substrate is a glycated amino acid, a glycated peptide or a glycated protein, for example, there is a difference between the case where an α-amino group is glycated and the case where an amino group other than the α-amino group is glycated.

In Formula (1), when an a-amino group is glycated, $R^2$ is an amino acid residue or a peptide residue represented by Formula (2) below.

$$—CHR^3—CO—R^4 \quad (2)$$

In Formula (2), $R^3$ denotes an amino-acid side chain group. $R^4$ denotes a hydroxyl group, an amino acid residue or a peptide residue, and can be represented, for example, by Formula (3) below. In Formula (3), n is an integer of 0 or larger, and $R^3$ denotes an amino-acid side chain group as in the above.

$$—(NH—CHR^3—CO)_n—OH \quad (3)$$

In Formula (1) above, when an amino group other than the cc-amino group is glycated (i.e., an amino-acid side chain group is glycated), $R^2$ can be represented by Formula (4) below.

In Formula (4) above, $R^5$ denotes a portion other than the glycated amino group in the amino-acid side chain group. For example, when the glycated amino acid is lysine, $R^5$ is as follows.

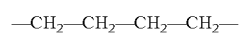

For another example, when the glycated amino acid is arginine, $R^5$ is as follows.

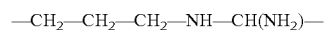

In Formula (4) above, $R^6$ denotes hydrogen, an amino acid residue or a peptide residue, and can be represented, for example, by Formula (5) below. In Formula (5), n denotes an integer of 0 or lager, and $R^3$ denotes an amino-acid side chain group as in the above.

$$—(CO—CHR^3—NH)_n—H \quad (5)$$

In Formula (4) above, $R^7$ denotes a hydroxyl group, an amino acid residue or a peptide residue, and can be represented, for example, by Formula (6) below. In Formula (6), n is an integer of 0 or lager, and $R^3$ denotes an amino-acid side chain group as in the above.

$$—(NH—CHR^3—CO)_n—OH \quad (6)$$

In the following, the method of measuring a glycated protein according to the present invention will be described by way of specific examples. It should be noted that the present invention is by no means limited by an embodiment below.

First Embodiment

The method of measuring a glycated protein according to the present invention will be described with reference to examples in which an analyte is a glycated protein in blood cells.

First, whole blood itself is hemolyzed, or a blood cell fraction is separated from whole blood in the usual way such as centrifugation and then hemolyzed, so as to prepare a hemolyzed sample. The method of causing the hemolysis is not particularly limited and can be, for example, a method using a surfactant, a method using ultrasonic waves, a method utilizing a difference in osmotic pressure or the like. Among these, the method using a surfactant is preferable.

The surfactant for hemolysis is not particularly limited, and examples thereof include nonionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants) and the like. Specific examples thereof are trade name Triton X-100, trade name Tween-20, trade name Brij 35, etc. The conditions of the treatment with the surfactant usually are as follows: when the concentration of blood cells in the solution to be treated is 1 to 10 vol %, the surfactant is added so that its concentration in the solution falls in the range from 0.1 to 1 wt %, and stirred at room temperature for about 5 seconds to 1 minute.

In the case of utilizing the difference in osmotic pressure, the hemolysis can be carried out by, for example, adding purified water in a volume that is 2 to 100 times as much as the whole blood.

Next, the hemolyzed sample is treated with the protease in the presence of the sulfonic acid compound so as to degrade the glycated protein, thus preparing a glycated protein degradation product. The reason why the glycated protein is treated with the protease as described above follows. Considering the fact that the FAOD to be used in the subsequent process is unlikely to act on proteins and long polypeptide chains as described earlier, these proteins and long polypeptide chains are degraded so that the FAOD can act on the glycated portions more easily. Since the protease treatment in the presence of the sulfonic acid compound can degrade the glycated protein within a short time and with a high degradation efficiency as described above, even a short period of the protease treatment allows the FAOD to act on the glycated portion sufficiently. To further accelerate the degradation, the treatment may be carried out in the presence of the sulfonic acid compound and the nitro compound as described later.

The protease treatment usually is carried out in a buffer. The kind of the buffer is not particularly limited but can be, for example, a tris-hydrochloric acid buffer, an EPPS buffer, a PIPES buffer, a phosphate buffer, an ADA buffer, a citrate buffer, an acetate buffer, a glycinamide buffer, a CHES buffer or the like. The pH thereof preferably ranges from 5 to 12, more preferably from 6 to 10, and particularly preferably from 7 to 9.

As the protease, for example, protease K, subtilisin, trypsin, aminopeptidase and the like can be used as described above. The ratio of the protease to be added is as follows: for example, when the concentration of blood cells in the solution to be treated is 0.1 to 10 vol %, the protease is added so that its ratio in the solution ranges preferably from 0.1 to 100 g/L, more preferably from 0.3 to 50 g/L and particularly preferably from 0.5 to 20 g/L.

In the case where the glycated protein to be degraded is glycated hemoglobin, it is preferable to use as the protease a protease degrading the glycated hemoglobin selectively, e.g., bromelain, papain, trypsin derived from porcine pancreas, metalloproteinase, and protease derived from *Bacillus subtilis*, as described earlier. The ratio of the protease to be added is as follows: for example, when the concentration of blood cells in the solution to be treated is 0.1 to 10 vol %, the protease is added so that its ratio in the solution ranges preferably from 0.1 to 50 g/L, more preferably from 0.3 to 30 g/L and particularly preferably from 1 to 20 g/L. More specifically, when the protease is metalloproteinase, it preferably is added to the solution with a blood cell concentration of 0.3 to 5 vol % so that its ratio in the solution ranges from 0.1 to 30 g/L, more preferably from 0.3 to 20 g/L and particularly preferably from 1 to 10 g/L.

The ratio of the sulfonic acid compound to be added is as follows: for example, when the concentration of blood cells in the solution to be treated with the protease is 1 vol %, the sulfonic acid compound is added so that its concentration in the solution ranges preferably from 0.0001 to 100 mmol/L, more preferably from 0.0003 to 60 mmol/L and particularly preferably from 0.001 to 30 mmol/L. More specifically, when the sulfonic acid compound is SLS and the blood cell concentration in the solution to be treated with the protease is 1 vol %, the sulfonic acid compound preferably is added to the solution so that its concentration in the solution ranges from 0.1 to 100 mmol/L, more preferably from 0.2 to 60 mmol/L and particularly preferably from 0.5 to 30 mmol/L.

Although the sulfonic acid compound may be used as it is, it preferably is dissolved in a solvent and used as a sulfonic acid compound solution in view of simplicity of operation and treatment efficiency. The concentration of this solution can be determined suitably depending on the kind of the sulfonic acid compound or the like and ranges, for example, from 1 to 1000 mmol/L. As the solvent, it is possible to use distilled water, a physiological salt solution, buffers and the like, and the buffer can be any of those listed above, for example. Incidentally, the above-mentioned sulfonic acid compound may be one kind or a combination of two or more.

The conditions of the protease treatment in the presence of the sulfonic acid compound are not particularly limited but, for example, are as follows: the temperature ranges from 10° C. to 37° C., and the treating period ranges from 30 seconds to 60 minutes. The temperature preferably ranges from 20° C. to 37° C., and the treating period preferably ranges from 30 seconds to 10 minutes. The former more preferably ranges from 25° C. to 37° C., and the latter more preferably ranges from 30 seconds to 5 minutes.

The protease treatment of a sample in the presence of the sulfonic acid compound in this manner can further accelerate the degradation of the glycated protein in the sample, so that the degradation product of the glycated protein can be obtained within a short time and with a high degradation efficiency.

Also, by carrying out this protease treatment in the presence of not only the sulfonic acid compound but also the nitro compound, the degradation with the protease can be accelerated further.

The ratio of the nitro compound to be added is not particularly limited but can be determined suitably depending on, for example, the amount of the sulfonic acid compound to be added, the amount of protease, etc. When the blood cell concentration in the solution to be treated with the protease is 1 vol %, the nitro compound is added so that, for example, its concentration in the solution ranges preferably from 0.01 to 25 mmol/L and more preferably from 0.05 to 10 mmol/L.

Next, the degradation product obtained by the protease treatment is treated with the FAOD. This FAOD treatment catalyzes the reaction shown by Formula (1) above.

It is preferable that the FAOD treatment is carried out in a buffer as in the above protease treatment. The conditions of the FAOD treatment are determined suitably depending on the kind of the FAOD used, the kind and concentration of the glycated protein as the analyte, etc.

More specifically, the conditions are as follows: the concentration of the FAOD in the reaction solution ranges from 50 to 50,000 U/L, the concentration of blood cells in the reaction solution ranges from 0.01 to 1 vol %, a reaction temperature ranges from 15° C. to 37° C., a reaction period ranges from 1 to 60 minutes, and a pH ranges from 6 to 9. Moreover, the kind of the buffer is not particularly limited, and for example, the buffers similar to those in the protease treatment can be used.

Subsequently, POD and the color-developing substrate are added to the hydrogen peroxide generated in the above FAOD treatment so as to allow the substrate to develop color, and the degree of the color developed is measured. When the POD is allowed to act on the hydrogen peroxide, the hydrogen peroxide is reduced and the color-developing substrate is oxidized so as to develop color. Since there is a correlation between the degree of color that the substrate has developed by oxidation and the amount of the generated hydrogen peroxide, the amount of the hydrogen peroxide can be determined by measuring the degree of the color developed.

The color-developing substrate can be substrates as described above and particularly preferably is N-(carboxymethylaminocarbonyl)-4,4'-bis(dimethylamino)diphenylamine sodium salt.

The color development reaction usually is carried out in a buffer. The conditions of the reaction are determined suitably depending on the concentration of the generated hydrogen peroxide, etc. The conditions are usually as follows: the concentration of the POD in the reaction solution ranges from 10 to 20,000 IU/L, the concentration of the color-developing substrate ranges from 0.001 to 1 mmol/l, a reaction temperature ranges from 20° C. to 37° C., a reaction period ranges from 1 to 5 minutes, and a pH ranges from 6 to 9. Moreover, the kind of the buffer is not particularly limited, and for example, the buffers similar to those in the protease treatment and the FAOD treatment can be used.

In the color development reaction, for example, when the color-developing substrate is used, the amount of the hydrogen peroxide can be determined by measuring the degree of the color developed (i.e. absorbance) in the reaction solution with a spectrophotometer. Then, using this concentration of the hydrogen peroxide and a calibration curve or the like, the amount of the glycated protein in the sample can be determined.

The amount of the hydrogen peroxide can be determined not only by the above-described enzymatic method using a POD or the like but also by an electrical method, for example.

With such a measuring method according to the present invention, it is possible to perform measurements quickly as described above. Also, the conventional method may suffer from a lowered accuracy of measurement when the protease treatment is shortened, whereas the measuring method of the present invention achieves a measurement with an excellent accuracy even within a short period.

EXAMPLES

Hereinafter, examples will be described together with comparative examples.

Example 1, Comparative example 1

In Example 1, glycated hemoglobin was treated with a protease in the presence of a sulfonic acid compound, thus measuring the degree of glycation of its degradation product using a color-developing substrate TPM-PS. The sample and reagents used here and the method will be described below. The sulfonic acid compound in a first reagent described below was SLS (manufactured by Nacalai Tesque, Inc.).

(Preparation of Sample to be Measured)

Lyophilized hemoglobin was dissolved in purified water, thus preparing a hemoglobin solution with a hemoglobin concentration of 50 g/L and a HbA1c concentration of 6.5% (HbA1c: Low) and a hemoglobin solution with a hemoglobin concentration of 50 g/L and a HbA1c concentration of 11.5% (HbA1c: High). Then, 60 μL of each of these hemoglobin solutions was mixed with 240 μL of purified water so as to prepare a sample with a HbA1c concentration of 6.5% (hereinafter, referred to as a "sample Low") and a sample with a HbA1c concentration of 11.5% (hereinafter, referred to as a "sample High").

(First Reagent)

| | |
|---|---|
| Sulfonic acid compound | 6.4 mM |
| Surfactant (polyoxyethylene(9)dodecyl ether) | 1.85 g/L |
| CHES-CHES · Na buffer (pH 9.4) | 40 mM |
| MOPS-MOPS · Na buffer (pH 9.4) | 15 mM |

(Second Reagent)

| | |
|---|---|
| Metalloproteinase (manufactured by ARKRAY, INC.) | 2.0 MU/L |
| CaCl$_2$ | 2.5 mM |
| NaCl | 50 mM |
| MOPS-MOPS · Na buffer (pH 6.5) | 1.0 mM |

(Third Reagent)

| | |
|---|---|
| FAOD (manufactured by ARKRAY, INC.) | 18 KU/L |
| POD (manufactured by Kikkoman Corporation) | 67 KU/L |
| TPM-PS (manufactured by DOJINDO LABORATORIES) | 0.25 mM |
| Tris-HCl buffer (pH 7.0) | 300 mM |

(Method)

Measurement was carried out for each of the sample Low and the sample High. First, after 8.26 μL of the first reagent was added to 0.14 μL of the sample to be measured, 75.6 μL of the second reagent further was mixed therein and allowed to stand at 37° C. for 5 minutes. Then, 18.9 μL of the third reagent was blended into this mixture and incubated at 37° C. so as to allow a color development reaction. The absorbance of the reaction solution 2.5 minutes after adding the third reagent was measured with trade name JCA-BM8 (manufactured by JEOL. Ltd.). The measurement wavelengths were set to 571 nm for the main wavelength and 805 nm for the sub-wavelength. On the other hand, in the Comparative Example, the absorbance was measured similarly to Example 1 described above except that the sulfonic acid compound in the first reagent was not added. When the first reagent and the second reagent were mixed into the sample, the amount of the added sulfonic acid compound was 0.378 μmol with respect to 1 μL of the sample.

TABLE 1

| | Sulfonic acid compound (mM) | Nitro compound (mM) | Absorbance | | |
|---|---|---|---|---|---|
| | | | Sample High (mAbs) | Sample Low (mAbs) | High − Low (mAbs) |
| Example 1 | SLS (6.4) | — | 51.0 | 34.0 | 17.0 |
| Comparative example 1 | — | — | 16.7 | 16.0 | 0.7 |

As shown in Table 1 above, in Example 1, the absorbance of the sample High and the absorbance of the sample Low respectively were higher than those of the Comparative Example. This is because, by the protease treatment in the presence of the sulfonic acid compound, the degradation of the glycated hemoglobin was accelerated, so that the FAOD could act on glycated portions more easily. In other words, according to Example 1, the acceleration of the degradation allowed the FAOD to act easily on more glycated portions than the Comparative Example, thus improving the accuracy of measurement.

Further, in Example 1, the difference between the absorbance of the sample High and that of the sample Low was greater than that in the Comparative Example. The sample High had a hemoglobin concentration equal to the sample Low but had a higher HbA1c concentration than the sample Low. In other words, because of a greater glycated amount of hemoglobin, the sample High theoretically had an absorbance greater than the sample Low in proportion to the HbA1c concentration. However, in the Comparative Example, since the protease treatment was carried out in the absence of the sulfonic acid compound, the glycated hemoglobin was difficult to degrade. Therefore, even though the sample High and the sample Low had different HbA1c concentrations, their difference in absorbance was as small as 0.7 mAbs. On the other hand, in the Example where the protease treatment was carried out in the presence of the sulfonic acid compound, the difference between the absorbance of the sample High and that of the sample Low increased to about twenty times to thirty times that in the Comparative Example. This also shows that, for the same reason as above, the method according to Example 1 improved the sensitivity and accuracy of measurement.

Example 2

In Example 2, glycated hemoglobin was treated with a protease in the presence of a sulfonic acid compound, thus measuring the degree of glycation of its degradation product using a color-developing substrate DA-64. The sample and reagents used here and the method will be described below.

(First Reagent)

| | |
|---|---|
| Sulfonic acid compound (SLS: manufactured by Nacalai Tesque, Inc.) | 6.4 mM |
| Surfactant (polyoxyethylene(9)dodecyl ether) | 1.85 g/L |
| CHES-CHES · Na buffer (pH 9.4) | 40 mM |
| MOPS-MOPS · Na buffer (pH 9.4) | 15 mM |

(Second Reagent)

| | |
|---|---|
| Nitro compound | 0.9 mM or 1.8 mM |
| Metalloproteinase (manufactured by ARKRAY, INC.) | 2.0 MU/L |
| CaCl$_2$ | 2.5 mM |
| NaCl | 50 mM |
| MOPS-MOPS · Na buffer (pH 6.5) | 1.0 mM |

As the nitro compound, 2,4-DNA (manufactured by Wako Pure Chemical Industries, Ltd.), p-NA (manufactured by Wako Pure Chemical Industries, Ltd.), p-NP (manufactured by Wako Pure Chemical Industries, Ltd.), NaNO2 (manufactured by Nacalai Tesque, Inc.) and 2,4-DNH (manufactured by Wako Pure Chemical Industries, Ltd.) were used individually. In the case of adding two kinds of the nitro compound, the concentration was 1.8 mM in total (0.9 mM each).

(Third Reagent)

| | |
|---|---|
| FAOD (manufactured by ARKRAY, INC.) | 18 KU/L |
| POD (manufactured by Kikkoman Corporation) | 67 KU/L |
| DA-64 (manufactured by Wako Pure Chemical Industries, Ltd.) | 70 μM |
| Tris-HCl buffer (pH 7.0) | 300 mM |

(Method)

Measurement was carried out for each of the sample Low and the sample High that were prepared in Example 1 described above. After 8.26 μL of the first reagent was added to 0.14 μL of the sample to be measured, 75.6 μL of the second reagent further was mixed therein and allowed to stand at 37° C. for 5 minutes. Then, 18.9 μL of the third reagent was blended into this mixture and incubated at 37° C. so as to allow a color development reaction. The absorbance after 5 minutes was measured with trade name JCA-BM8 (manufactured by JEOL. Ltd.). The measurement wavelengths were set to 751 nm for the main wavelength and 805 nm for the sub-wavelength. On the other hand, in Comparative example 2, the absorbance was measured similarly to Example 1 described above except that the sulfonic acid compound in the first reagent and the nitro compound in the second reagent were not added. The results are shown in Table 2 below. In Table 2, "High-Low (mAbs)" is a value obtained by subtracting the absorbance of the sample Low from that of the sample High.

TABLE 2

| Example | Sulfonic acid compound (mM) | Nitro compound (mM) | Absorbance | | |
|---|---|---|---|---|---|
| | | | Sample High (mAbs) | Sample Low (mAbs) | High − Low (mAbs) |
| 2-1 | SLS (6.4) | 2,4-DNA (0.9) | 4.2 | 1.6 | 2.6 |
| 2-2 | SLS (6.4) | p-NA (0.9) | 2.6 | 1.2 | 1.4 |
| 2-3 | SLS (6.4) | p-NP (0.9) | 3.2 | 1.6 | 1.6 |
| 2-4 | SLS (6.4) | NaNO$_2$ (0.9) | 2.3 | 1.3 | 1.0 |
| 2-5 | SLS (6.4) | 2,4-DNA (0.9) p-NA (0.9) | 3.5 | 1.6 | 1.9 |
| 2-6 | SLS (6.4) | 2,4-DNA (0.9) p-NA (0.9) | 2.8 | 1.1 | 1.7 |
| 2-7 | SLS (6.4) | p-NP (0.9) p-NA (0.9) | 3.3 | 1.3 | 2.0 |
| 2-8 | SLS (6.4) | 2,4-DNA (0.9) NaN$_3$ (0.9) | 4.0 | 1.9 | 2.1 |

TABLE 2-continued

| Example | Sulfonic acid compound (mM) | Nitro compound (mM) | Absorbance | | |
|---|---|---|---|---|---|
| | | | Sample High (mAbs) | Sample Low (mAbs) | High – Low (mAbs) |
| Comp. example 2 | — | — | 1.1 | 0.9 | 0.2 |

As shown in Table 2 above, in Example 2, the absorbance of the sample High and the absorbance of the sample Low respectively were higher than those of the Comparative Example, similarly to Example 1. Also, the difference between the absorbance of the sample High and that of the sample Low was greater than that in Comparative Example 2. These results show that, similarly to Example 1 above, by the protease treatment in the presence of the sulfonic acid compound and the nitro compound, the degradation of the glycated hemoglobin was accelerated, thus improving the sensitivity and accuracy of measurement.

INDUSTRIAL APPLICABILITY

As described above, in accordance with the measuring method according to the present invention, by a protease treatment in the presence of the sulfonic acid compound, proteins and the like can be degraded within a short time, thus allowing a quick measurement of glycated proteins and the like. This makes it possible to achieve a measurement with a still higher accuracy, and accordingly, the measuring method according to the present invention is useful for various tests in clinical medicine as described above.

The invention claimed is:

1. A method of measuring the amount of a glycated protein in a sample, the method comprising:
treating a sample containing the glycated protein with a protease in the presence of a sulfonic acid compound and a nitro compound to accelerate the degradation of the glycated protein,
adding a fructosyl amino acid oxidase to react in a redox reaction with a glycated portion of a glycated protein degradation product obtained by the protease treatment, and
measuring the redox reaction,
wherein the sulfonic acid compound is at least one selected from the group consisting of
4-aminoazobenzene-4'-sulfonic acid sodium salt,
4-amino-4'-nitrostilbene-2,2'-disulfonic acid disodium salt,
4,4'-diazidostilbene-2,2'-disulfonic acid disodium salt,
N-cyclohexyl-2-aminoethane sulfonic acid,
N-cyclohexyl-3-aminopropane sulfonic acid,
N-cyclohexyl-2-hydroxy-3-aminopropane sulfonic acid,
piperazine-1,4-bis(2-ethane sulfonic acid) and
bathophenanthroline sulfonic acid,
wherein the nitro compound is at least one selected from the group consisting of
2,4-dinitrophenol,
2,5-dinitrophenyl,
2,6-dinitrophenyl,
4,6-dinitro-2-methyl phenol,
2-amino-4-nitrophenol,
2-amino-5-nitrophenol,
2-amino-4-nitrophenol,
p-nitrophenol,
2,4-dinitroaniline,
p-nitroaniline,
4-amino-4'-nitrostilbene-2,2'-disulfonic acid disodium salt and nitrobenzene,
wherein the redox reaction is measured by determining an amount of hydrogen peroxide generated by the reaction of the glycated portion of the glycated protein degradation product and the frucytosyl amino acid oxidase, and
wherein the amount of the hydrogen peroxide is determined by using an oxidase to reduce the generated hydrogen peroxide and oxidize a substrate that develops color by oxidation and measuring a degree of the color that the substrate has developed.

2. The method according to claim 1, wherein the protease is a metalloproteinase.

3. The method according to claim 1, wherein the degree of the color is measured by measuring an absorbance at a wavelength for detecting the substrate.

* * * * *